United States Patent
Thorarensen

(10) Patent No.: US 6,620,810 B2
(45) Date of Patent: Sep. 16, 2003

(54) 4-THIOXO-4,7-DIHYDRO-THIENO[2,3-B] PYRIDINE-5-CARBOXAMIDES AS ANTIVIRAL AGENTS

(75) Inventor: Atli Thorarensen, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/230,890

(22) Filed: Aug. 29, 2002

(65) Prior Publication Data

US 2003/0109542 A1 Jun. 12, 2003

Related U.S. Application Data

(60) Provisional application No. 60/316,108, filed on Aug. 30, 2001.

(51) Int. Cl.[7] ............... A61K 31/5377; A61P 31/22; C07D 495/04
(52) U.S. Cl. ............ 514/233.8; 544/127; 544/58.6; 546/114
(58) Field of Search .............. 544/127; 546/114; 514/233.8

(56) References Cited

U.S. PATENT DOCUMENTS

| | | |
|---|---|---|
| 4,125,611 A | 11/1978 | Yamade et al. |
| 4,145,418 A | 3/1979 | Kuwada et al. |
| 4,767,766 A | 8/1988 | Baker et al. |
| 4,959,363 A | 9/1990 | Wentland |
| 5,593,943 A | 1/1997 | Nuebling et al. |
| 5,817,819 A | 10/1998 | Furuya et al. |

FOREIGN PATENT DOCUMENTS

| | | |
|---|---|---|
| DE | 4227747 | 2/1994 |
| EP | 0443568 A1 | 8/1991 |
| EP | 505058 | 9/1992 |
| JP | 07076586 A | 3/1995 |
| JP | 08301849 A | 11/1996 |
| JP | 9208496 | 8/1997 |
| WO | WO-92/03427 | 3/1992 |
| WO | WO-95/28405 | 10/1995 |
| WO | WO-96/18616 | 6/1996 |
| WO | WO-96/18617 | 6/1996 |
| WO | WO-97/40846 | 11/1997 |
| WO | WO-98/11073 | 3/1998 |
| WO | WO-99/62908 | 12/1999 |
| WO | WO-00/53610 | 9/2000 |

OTHER PUBLICATIONS

*Chemical Abstracts*, Abstract of German Patent No. 2,447,477, Abstract No. 85:46627,(Apr. 15, 1976),2 p.

El–Abadelah, Mustafa.M. ,et al. , "Synthesis and Chiroptical Properties of Some N–(2–Chloro–7–cyclopropyl–4,7–dihydro–4–oxo–thieno[2,3–b]pyridine–5–carbonyl) L–a–Amino Esters", *Zeitschrift fur Naturforschung B, A Journal of Chemical Sciences, 52(3)*,(1997),pp. 419–426.

Blaskiewicz, P..,et al. , "Thienopyridinonecarboxylic Acid Derivatives".

*Primary Examiner*—Robert W. Ramsuer
(74) *Attorney, Agent, or Firm*—Schwegman, Lundberg, Woessner & Kluth, P.A.

(57) ABSTRACT

The invention provides a compound of formula I:

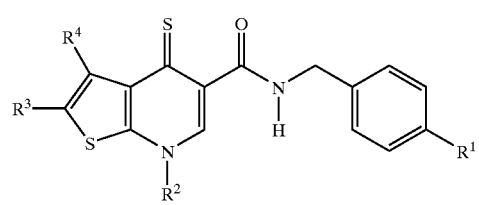

wherein $R^1$, $R^2$, $R^3$, and $R^4$ have any of the values defined in the specification, or a pharmaceutically acceptable salt thereof, as well as processes and intermediates useful for preparing such compounds or salts, and methods of treating a herpesvirus infection, atherosclerosis or restenosis using such compounds or salts.

30 Claims, No Drawings

4-THIOXO-4,7-DIHYDRO-THIENO[2,3-B] PYRIDINE-5-CARBOXAMIDES AS ANTIVIRAL AGENTS

RELATED APPLICATIONS

This applications claims priority to U.S. Provisional Patent Application No. 60/316,108, filed Aug. 30, 2001, which is incorporated herein by reference.

FIELD OF THE INVENTION

The present invention provides 4-thioxo-4,7-dihydro-thieno[2,3-b]pyridine-5-carboxamide derivatives, more specifically, 5-benzylaminocarbonyl-4-thioxo-4,7-dihydro-thieno[2,3-b]pyridine derivatives of formula (I), which are useful as antiviral agents (e.g. as agents against viruses of the herpes family).

BACKGROUND OF THE INVENTION

The herpes viruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Infection by or reactivation of herpes viruses is also associated with several cardiovascular diseases or conditions in the host such as atherosclerosis and restenosis resulting in inflammation of coronary vessel walls. It is thought that in many patients suffering from restenosis following coronary atherectomy, viral infection, particularly by CMV, plays an important role in the proliferation of the disease. Atherosclerosis is believed to be associated with the overall infectious disease burden in the host and particularly by the herpesvirus such as HSV, CMV, and EBV. Infection in the animal population (livestock and companion) by strains of herpesviruses is endemic including cattle (Bovine herspesvirus 1–5, BHV), sheep (Ovine herpesvirus 1 and 2), dog (Canine herpesvirus 1), horse (Equine herpesvirus 1–8, EHV), cat (Feline herpesvirus 1, FHV), swine (pseudorabies virus, PRV), and many species of fowl. In the case of bovine herpesvirus infection, animals may suffer from ocular, respiratory, or digestive disorders. Pseudorabies is an extremely contagious viral pathogen infecting several species such as cattle, horses, dogs, cats, sheep, and goats leading to rapid death. The virus is benign in adult swine, however, it remains contagious and leads to high mortality in pigs under three weeks. Infection of horses by equine herpesvirus may lead to neurological syndromes, respiratory disease, and neonatal disease. Herpesvirus infection in cats leads to the disease known as feline viral rhinotracheitis (FVR) which is characterized by rhinitis, tracheitis, laryngitis, and conjunctivitis.

SUMMARY OF THE INVENTION

The present invention provides a compound of formula I:

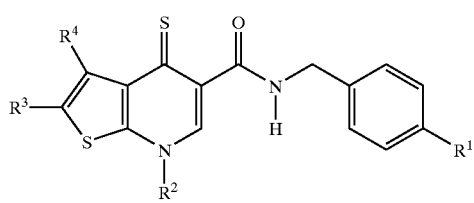

or a pharmaceutically acceptable salt thereof, wherein:

$R^1$ is
  (a) Cl,
  (b) Br,
  (c) CN,
  (d) $NO_2$, or
  (e) F;

$R^2$ is
  (a) H,
  (b) $R^5$,
  (c) $NR^7R^8$,
  (d) $SO_2R^9$, or
  (e) $OR^9$;

$R^3$ is
  (a) H,
  (b) halo,
  (c) aryl,
  (d) $S(O)mR^6$,
  (e) $(C=O)R^6$,
  (f) $(C=O)OR^9$,
  (g) cyano,
  (h) het, wherein said het is bound via a carbon atom,
  (i) $OR^{10}$,
  (j) Ohet,
  (k) $NR^7R^8$
  (l) $SR^{10}$,
  (m) Shet,
  (n) $NHCOR^{12}$,
  (o) $NHSO_2R^{12}$, or
  (p) $C_{1-7}$alkyl which may be partially unsaturated and optionally substituted by one or more substituents of the group $R^{11}$, $OR^{13}$, $SR^{10}$, $SR^{13}$, $NR^7R^8$, halo, $(C=O)C_{1-7}$alkyl, or $SO_mR^9$;

$R^4$ is
  (a) H,
  (b) halo,
  (c) $C_{1-4}$alkyl, or
  (d) $R^4$ together with $R^3$ form a carbocyclic or het, either of which may be optionally substituted by $NR^7R^8$, by $C_{1-7}$alkyl which may be optionally substituted by $OR^{14}$, or by het, wherein said het is bound via a carbon atom;

$R^5$ is
  (a) $(CH_2CH_2O)_iR^{10}$,
  (b) het, wherein said het is bound via a carbon atom,
  (c) aryl,
  (d) $C_{1-7}$alkyl which may be partially unsaturated and is optionally substituted by one or more substituents selected from a group consisting of $NR^7R^8$, $R^{11}$, $SO_mR^9$, and $OC_{2-4}$alkyl which may be further substituted by het, $OR^{10}$, or $NR^7R^8$, or
(e) $C_{3-8}$cycloalkyl which may be partially unsaturated and optionally substituted by one or more substituents selected from a group consisting of $R^{11}$, $NR^7R^8$, $SO_mR^9$, and $C_{1-7}$alkyl optionally substituted by $R^{11}$, $NR^7R^8$, or $SO_mR^9$;

$R^6$ is
(a) $C_{1-7}$alkyl,
(b) $NR^7R^8$,
(c) aryl, or
(d) het, wherein said het is bound via a carbon atom;

$R^7$ and $R^8$ are independently
(a) H,
(b) aryl,
(c) $C_{1-7}$alkyl which may be partially unsaturated and is optionally substituted by one or more substituents selected from a group consisting of $NR^{10}R^{10}$, $R^{11}$, $SO_mR^9$, $CONR^{10}R^{10}$, or halo, or,
(d) $R^7$ and $R^8$ together with the nitrogen to which they are attached form ahet;

$R^9$ is
(a) aryl,
(b) het,
(c) $C_{3-8}$cycloalkyl, or
(d) $C_{1-7}$alkyl which may be partially unsaturated and is optionally substituted by one or more substituents selected from a group consisting of $NR^{10}R^{10}$, $R^{11}$, SH, $CONR^{10}R^{10}$, or halo;

$R^{10}$ is
(a) H, or
(b) $C_{1-7}$alkyl optionally substituted by OH;

$R^{11}$ is
(a) $OR^{10}$,
(b) Ohet,
(c) Oaryl,
(d) $CO_2R^{10}$,
(e) het,
(f) aryl, or
(g) CN;

$R^{12}$ is
(a) H,
(b) het,
(c) aryl,
(d) $C_{3-8}$cycloalkyl, or
(e) $C_{1-7}$alkyl optionally substituted by $NR^7R^8$ or $R^{11}$;

$R^{13}$ is
(a) $(P=O)(OR^{14})_2$,
(b) $CO(CH_2)_nCON(CH_3)$—$(CH_2)_nSO_3^-M^+$,
(c) an amino acid,
(d) C(=O)aryl, or
(e) $C(=O)C_{1-7}$alkyl optionally substituted by $NR^7R^8$, aryl, het, $CO_2H$, or $O(CH_2)_nCO_2R^{14}$);

$R^{14}$ is
(a) H, or
(b) $C_{1-7}$alkyl;

each i is independently 2, 3, or 4;
each n is independently 1, 2, 3, 4 or 5;
each m is independently 0, 1, or 2;
M is sodium, potassium, or lithium;
wherein any aryl is optionally substituted with one or more substituents selected from the group consisting of halo, OH, cyano, $CO_2R^{14}$, $CF_3$, $C_{1-6}$alkoxy, and $C_{1-6}$alkyl which maybe further substituted by one to three $SR^{14}$, $NR^{14}R^{14}$, $OR^{14}$, het, or $CO_2R^{14}$; and wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$alkyl which maybe further substituted by one to three $SR^{14}$, $NR^{14}R^{14}$, $OR^{14}$, or $CO_2R^{14}$.

In another aspect, the present invention also provides:
a pharmaceutical composition comprising a compound of formula I, or a pharmaceutically acceptable salt thereof, and a pharmaceutically acceptable excipient (the composition preferably comprises an effective antiviral amount of the compound or salt);

a method of treating a herpesviral infection, comprising administering to a mammal (e.g. a human) in need of such treatment, a compound of formula (I) or a pharmaceutically acceptable salt thereof;

a method for treating atherosclerosis or restenosis, comprising administering to a mammal in need of such treatment, an effective amount of a compound of formula (I), or a pharmaceutically acceptable salt thereof;

a compound of formula (I) or a pharmaceutically acceptable salt thereof for use in medical treatment (e.g. the treatment of a herpesviral infection, atherosclerosis or restenosis);

the use of a compound of formula (I) or a pharmaceutically acceptable salt thereof to prepare a medicament for treating a herpesviral infection in a mammal (e.g. a human);

the use of a compound of formula (I) or a pharmaceutically acceptable salt thereof to prepare a medicament for treating atherosclerosis or restenosis in a mammal (e.g. a human); and a method for inhibiting a viral DNA polymerase, comprising contacting (in vitro or in vivo) the polymerase with an effective inhibitory amount of a compound of formula I, or a pharmaceutically acceptable salt thereof.

The invention also provides novel intermediates and processes disclosed herein that are useful for preparing compounds of formula I.

Compounds of formula I have a 4-substituted benzylaminocarbonyl substituent at the 5-position of the thieno[2,3-b]pyridine ring system. This substitution pattern has been found to provide compounds with significantly improved antiviral activity compared to thienopyridines lacking this substitution.

DETAILED DESCRIPTION OF THE INVENTION

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

Aryl denotes a phenyl radical or an ortho-fused bicyclic carbocyclic radical having about nine to ten ring atoms in which at least one ring is aromatic. Het is a four- (4), five- (5), six- (6), or seven- (7) membered saturated or unsaturated heterocyclic ring having 1, 2, 3, or 4 heteroatoms selected from the group consisting of oxy, thio, sulfinyl, sulfonyl, and nitrogen, which is optionally fused to a benzene ring, or any bicyclic heterocycle group. Het includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

When $R^4$ together with $R^3$ form a carbocyclic, $R^4$ and $R^3$ together can be a 2, 3, 4, 5, or 6 membered saturated or unsaturated carbon chain, which chain can optionally be fused to a benzene ring.

"Amino acid," includes a residue of natural amino acid (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, garnma-carboxyglutamate; hippuric acid, octahydroindole-2-carboxylic acid, statine, 1,2,3,4,-tetrahydroisoquinoline-3-carboxylic acid, penicillamine, omithine, citruline, α-methyl-alanine, para-benzoylphenylalanine, phenylglycine, propargylglycine, sarcosine, and tert-butylglycine). An amino acid can conveniently be linked to the remainder of a compound of formula I through the carboxy terminus, the amino terminus, or through any other convenient point of attachment, such as, for example, through the sulfur of cysteine. In particular, an amino acid can conveniently be linked to the remainder of a compound of formula I through the carboxy terminus.

"Treating" includes (i) preventing a pathologic condition from occurring (e.g. prophylaxis); (ii) inhibiting the pathologic condition or arresting its development; and (iii) relieving the pathologic condition.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art. In particular, it is understood that compounds of formula I wherein $R^2$ is hydrogen can exist in the corresponding tautomeric "enol" form, and that such tautomers are included as compounds of the invention.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula I having any combination of the values, specific values, more specific values, and preferred values described herein.

Specifically, $C_{1-7}$alkyl can be methyl, ethyl, propyl, isopropyl, butyl, iso-butyl, sec-butyl, pentyl, 3-pentyl, hexyl, or heptyl; $C_{3-8}$cycloalkyl can be cyclopropyl, cyclobutyl, cyclopentyl, cyclohexyl, cycloheptyl, or cyclooctyl; $C_{1-7}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; $C(=O)C_{1-7}$alkyl can be acetyl, propanoyl, butanoyl, pentanoyl, 4-methylpentanoyl, hexanoyl, or heptanoyl; aryl can be phenyl, indenyl, or naphthyl; het can be pyrrolidinyl, piperidinyl, morpholinyl, thiomorpholinyl, or heteroaryl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

When $C_{1-7}$alkyl is partially unsaturated, it can specifically be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

A specific value for Het is a five- (5), six- (6), or seven- (7) membered saturated or unsaturated ring containing 1, 2, 3, or 4 heteroatoms selected from the group consisting of non-peroxide oxy, thio, sulfinyl, sulfonyl, and nitrogen; as well as a radical of an ortho-fused bicyclic heterocycle of about eight to twelve ring atoms derived therefrom, particularly a benz-derivative or one derived by fusing a propylene, trimethylene, tetramethylene or another monocyclic het diradical thereto.

A specific value for $R^1$ is F, Cl, or Br.

A more specific value for $R^1$ is Cl.

A specific value for $R^2$ is H.

A specific value for $R^2$ is $R^5$, $NR^7R^8$, $SO_2R^9$, or $OR^9$.

A specific value for $R^2$ is $R^5$.

A more specific value for $R^2$ is methyl, ethyl, propyl, isopropyl, butyl, tert-butyl, carboxymethyl, (Cl $_{1-7}$ alkoxy) carbonylmethyl, 2-hydroxyethyl, 2-(2-methoxy-ethoxy) ethyl, 3-(2-tetrahydropyranyloxy)propyl, 2-morpholinoethyl, 2-(diethylamino)ethyl, 2-(dimethylamino)ethyl, 2-piperidinoethyl, 3-piperidinopropyl, 2-(1-methylpyrrolidin-2-yl)ethyl, 2-(diisopropylamino)ethyl, 2-pyrrolidin-1-ylethyl, 3-(dimethylamino)propyl, benzyl, 3-fluorobenzyl, 3-phenylpropyl, 2-tetrahydrofuranylmethyl, 2-pyrrolidinoethyl, 3-pyridylmethyl, or vinyl.

A more specific value for $R^2$ is methyl, ethyl, isopropyl, 2-hydroxyethyl, 2-(diethylamino)ethyl, or 2-(dimethylamino)ethyl.

A specific value for $R^3$ is H, halo, $S(O)_mR^6$, $(C=O)R^6$, $(C=O)OR^9$, cyano, or $C_{1-7}$alkyl which may be partially unsaturated and optionally substituted by one or more substituents of the group $R^{11}$, $OR^{13}$, $SR^{10}$, $SR^{13}$, $NR^7R^8$, halo, $(C=O)C_{1-7}$alkyl, and $SO_mR^9$.

A specific value for $R^3$ is $C_{1-7}$alkyl which may be partially unsaturated and optionally substituted by one or more substituents of the group $R^{11}$, $OR^{13}$, $SR^{10}$, $SR^{13}$, $NR^7R^8$, halo, $(C=O)C_{1-7}$alkyl, and $SO_mR^9$.

A specific value for $R^3$ is $C_{1-7}$alkyl which may be partially unsaturated and is substituted by one or more substituents of the group $R^{11}$, $OR^{13}$, $SR^{10}$, $SR^{13}$, $NR^7R^8$, halo, $(C=O)C_{1-7}$alkyl, and $SO_mR^9$.

A specific value for $R^3$ is $C_{1-7}$alkyl which may be partially unsaturated and is substituted by one or more substituents of the group $OR^{10}$, het and $NR^7R^8$.

A specific value for $R^3$ is (Z or E) —CH=CH(CH$_2$)$_n$R$_a$ or —C≡C(CH$_2$)$_n$R$_a$ wherein R$_a$ is $R^{11}$, $OR^{13}$, $SR^{10}$, $SR^{13}$, $NR^7R^8$, halo, $(C=O)C_{1-7}$alkyl, or $SO_mR^9$.

A more specific value for $R^3$ is bromo, iodo, 3-hydroxy-1-propynyl, 3-methoxy-1-propynyl, 4-hydroxy-1-butynyl, 3-hydroxypropyl, cyano, 4,4-di(methoxycarbonyl)-1-butynyl, 4-hydroxybutyl, 3-(3-carboxypropanoyloxy)-1-propynyl, 3-(morpholinoacetoxy)-1-propynyl, 3-(2-amino-3-methylbutanoyloxy)-1-propynyl, or thiomorpholinomethyl, N-[2-(4-hydroxyphenyl)-2-hydroxyethyl]-N-(methyl)aminomethyl, morpholinocarbonyl, 3-[3-(morpholinomethyl)benzoyloxy]-1-propynyl.

A more specific value for $R^3$ is iodo, 3-hydroxy-1-propynyl, 4-hydroxy-1-butynyl, 3-hydroxypropyl, morpholinomethyl, N-[2-(4-hydroxyphenyl)-2-hydroxyethyl]-N-(methyl)aminomethyl or 4-hydroxybutyl.

A specific value for $R^3$ is 3-hydroxy-1-propynyl, morpholinomethyl, N-[2-(4-hydroxyphenyl)-2-hydroxyethyl]-N-(methyl)aminomethyl or 3-hydroxypropyl.

A specific value for $R^5$ is $(CH_2CH_2O)_rR^{10}$.

A specific value for $R^5$ is $C_{1-7}$alkyl which may be partially unsaturated and is optionally substituted by one or more substituents selected from a group consisting of $NR^7R^8$, $R^{11}$, $SO_mR^9$, and $OC_{2-4}$alkyl, which may be further substituted by het, $OR^{10}$, or $NR^7R^8$; wherein $R^9$ and $R^{10}$ have any of the values defined herein; and wherein $R^7$ and $R^8$ are independently (a) H,
(b) aryl, or
(c) $C_{1-7}$alkyl which may be partially unsaturated and is optionally substituted by one or more substituents selected from a group consisting of $NR^{10}R^{10}$, $R^{11}$, $SO_mR^9$, $CONR^{10}R^{10}$, or halo; and, $R^{11}$ is
(a) $OR^{10}$,
(b) Ohet,
(c) Oaryl,
(d) $CO_2R^{10}$, or
(g) CN.

A specific value for $R^5$ is $C_{1-7}$alkyl which may be partially unsaturated and is optionally substituted by one or more substituents selected from a group consisting of $NR^7R^8$, $R^{11}$, $SO_mR^9$, and $OC_{2-4}$alkyl, which may be further substituted by het, $OR^{10}$, or $NR^7R^8$.

A specific value for $R^5$ is $C_{1-7}$alkyl, which may be partially unsaturated and is optionally substituted by one or more aryl or het.

A more specific value for $R^5$ is $C_{1-7}$alkyl.

A specific compound of formula I is a compound wherein any aryl, or het is optionally substituted with one or two substituents selected from the group consisting of halo, cyano, het, trifluoromethyl, trifluoromethoxy, hydroxy $C_{1-7}$alkoxy, and $C_{1-7}$alkyl; or a pharmaceutically acceptable salt thereof.

Preferred compounds of formula I exclude compounds disclosed specifically or generically in the references cited herein.

The preparation of starting materials and intermediate 4-oxo-compounds useful for preparing the thioxo compounds of the present invention are disclosed in U.S. Pat. No. 6,239,142 and International Patent Application Publication No. WO-00/53610. The 4-thioxo-compounds of the invention can be prepared from the intermediate 4-oxo-compounds using procedures similar to those illustrated in Charts A and B.

In Chart A, ketone-amide A-1 is reacted with Lawesson's reagent in the presence of KHMDS in refluxing toluene to furnish the thioketone-amide A-2:

CHART A

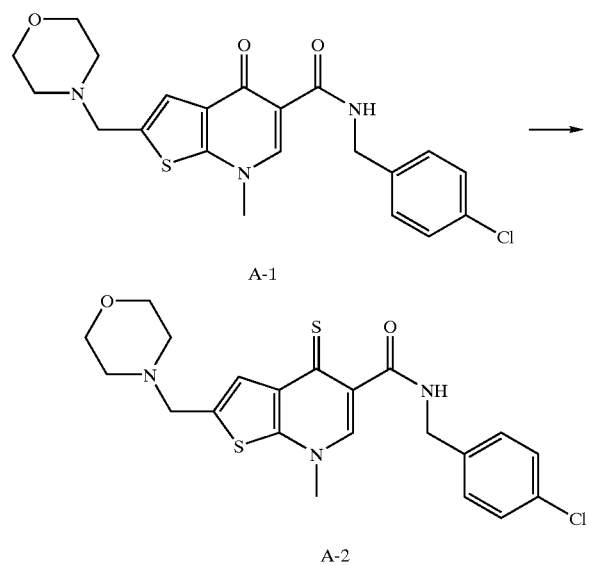

In Chart B, the hydroxypropyl compound B-1 is reacted in DMF with TIPSCl in the presence of imidiazole to afford the protected alcohol B-2 (In Wuts, P. G. *Protecting Groups in Organic Chemistry* 1999, 123). The ketone B-2 is reacted with Lawesson's reagent in the presence of KHMDS in refluxing toluene to furnish the protected alcohol thioketone-carboxamide B-3. The protected alcohol B-3 is then treated with Bu$_4$N$^+$F in THF affording the hydroxyl compound B-4 (In Wuts, P. G. *Protecting Groups in Organic Chemistry* 1999, 124).

CHART B

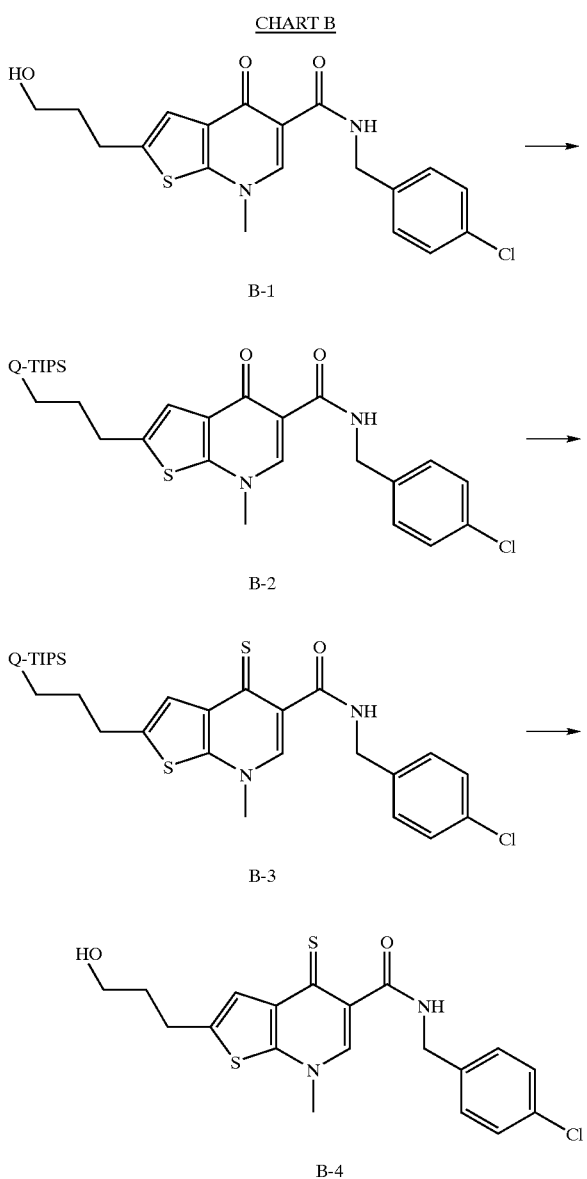

The invention also provides processes and intermediates described herein that are useful for preparing compounds of the invention. For example, the invention provides a method for preparing a thioxo compound of formula I:

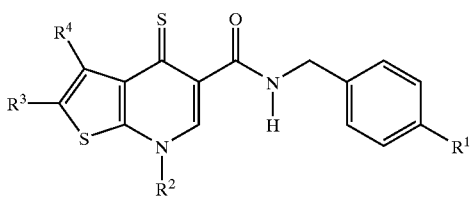

wherein $R^1$–$R^4$ have the above values, comprising reacting a corresponding oxo compound of the formula II:

Lawesson's Reagent (2,4-bis(4-methoxyphenyl)-1,3-dithia-2,4-diphosphetane-2,4-disulfide) to provide the compound of formula I. The above transformation can be similarly accomplished with other alternative or equivalent suitable thionating reagents, for example, $P_2S_5$, see Lightner, D.A. et al., *J. Am. Chem. Soc.*, 1984, 106, 934, and Spear, G. W. et al., *Synth. Commun.*, 2000, 30, 565; $P_4S_{10}$, see Hartke, K. et al., *J. Prakt, Chem./Chem-Ztg*, 1996, 338, 251; Belleau reagent, see Belleau, B. et al., *Tetrahedron Lett.*, 1983, 24, 3815; and polymer thionating reagent, see Ley, S. V. et al., *J. Chem. Soc. Perkin Trans.* 1., 2001, 358.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and x-glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt %, preferably from about 0.5–10 wt %. The concentration in a semi-solid or solid composition such as a gel or a powder will be about 0.1–5 wt-%, preferably about 0.5–2.5 wt %.

The exact regimen for administration of the compounds and compositions disclosed herein will necessarily be dependent upon the needs of the individual subject being treated, the type of treatment and, of course, the judgment of the attending practitioner.

The antiviral activity of a compound of the invention can be determined using pharmacological models which are well known to the art, or using Test A described below.

The compounds of formula (I) and pharmaceutically acceptable salts thereof are useful as antiviral agents. Thus, they are useful to combat viral infections in animals, including man. The compounds are generally active against herpes viruses, and are particularly useful against the varicella zoster virus, the Epstein-Barr virus, the herpes simplex virus, the human herpes virus type 8 (HHV-8) and the cytomegalovirus (CMV).

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

Test A.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 μl volume with 5.4 mM HEPES (pH 7.5), 11.7 mM KCl, 4.5 mM $MgCl_2$, 0.36 mg/ml BSA, and 90 nM $^3$H-dTTP. Assays are run with and without CHAPS, (3-[(3-cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 μg/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25 C or 37 C $H_2O$ bath and terminated via the addition of 40 μl/reaction of 0.5 M EDTA (pH 8) per well. Reactions are terminated within the timeframe during which substrate incorporation is linear and varied depending upon the enzyme and conditions used, i.e., 30 min. for HCMV polymerase. Ten μl of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and $IC_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing for a representative compound of formula I in this assay are shown in Table 1. In Table 1, the term "nd" refers to activity data not determined.

TABLE 1

| | Biological Data | | |
| --- | --- | --- | --- |
| | | polymerase $IC_{50}$ (μM) | |
| Example | HCMV | HSV | VZV |
| 1 | 0.63 | 0.16 | 0.08 |

DESCRIPTION OF PREFERRED EMBODIMENTS

The preparation of intermediate 4-oxo-compounds of formula II that can be converted to the corresponding 4-thioxo compounds of formula I of the present invention are disclosed in the above mentioned U.S. Pat. No. 6,239,142 and International Patent Application Publication No. WO-00/53610. The following examples provide representative preparations of the compounds of the present invention.

EXAMPLE 1

N-(4-chlorobenzyl)-7-methyl-2-(4-morpholinylmethyl)-4-thioxo-4,7-dihydrothieno[2,3-b]pyridine-5-carboxamide, (A-2 of Chart A)

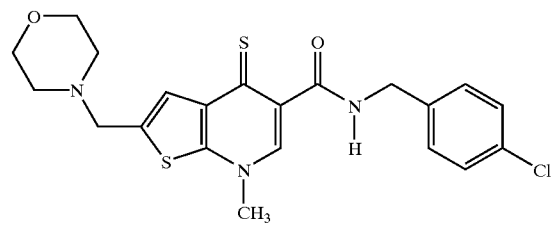

A-1 (570 mg, 1.32 mmol) was dissolved in dichloroethane (80 mL) followed by the addition of KHMDS (0.5 M, 2.64 mL, 1.32 mmol, 1 equiv.). Lawesson's reagent (1.1 g, 2.64 mmol, 2.0 equiv.) and toluene (80 mL) were added and the resulting mixture was heated at reflux for 6 hours. The reaction was cooled to room temperature, diluted with dichloromethane, washed with water, $Na_2CO_3$, brine, dried ($MgSO_4$), filtered and concentrated in vacuo. The residue was purified by silica gel chromatography (heptane/EtOAc 1/1, ¼, 0/1 then DCM/MeOH 19/1) to afford 248 mg of crude A-2, which was triturated with MeOH to afford 216 mg (37%) of the title compound as a tan solid.

Physical characteristics are as follows:

$^1$H NMR (TFA$_{d1}$) δ 8.94, 8.19, 7.40, 7.34, 5.02, 4.75, 4.47, 4.43, 4.18, 3.93, 3.65–3.62, $^{13}$C NMR (CDCl$_3$/DMSO) δ 179.91, 164.94, 145.11, 142.23, 142.00, 141.62, 138.34, 131.90, 129.36, 128.53, 126.70, 124.64, 114.48, 68.55, 57.24, 54.88, 53.40, 44.25, 42.52; IR 2296, 1906, 1654, 1579, 1546, 1508, 1491, 1348, 1270, 1150, 1132, 1114, 1004, 868, 822, cm$^{-1}$; MS (EI) m/z 447, 449, 447, 416, 415, 414, 195, 194, 86, 56, 32; HRMS (EI) calcd for $C_{21}H_{22}ClN_3O_2S_2$, 447.0842, found 447.0839. Anal. Calcd for $C_{21}H_{22}ClN_3O_2S_2$: C, 56.30; H, 4.95; N, 9.38; Cl, 7.91; S, 14.31; Found: C, 56.21; H, 4.97; N, 9.33.

EXAMPLE 2

N-(4-Chlorobenzyl)-7-methyl-2-(3-hydroxypropyl)-
4-thioxo-4,7-dihydrothieno[2,3-b]pyridine-5-
carboxamide (Chart B, B4)

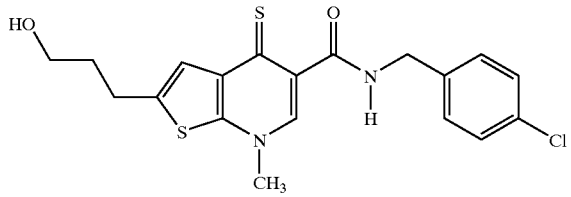

The hydroxypropyl compound B-1 (WO-00/53610) is reacted in DMF with TIPSCl in the presence of imidiazole to afford B-2. The ketone B-2 is reacted with Lawesson's reagent in the presence of KHMDS in refluxing toluene to firnish the protected alcohol thioketone-carboxamide B-3. The protected alcohol B-3 is then treated with $Bu_4N^+F$ in THF affording the hydroxyl compound B4.

EXAMPLE 3

Using procedures similar to those described herein, the following compounds of the invention can also be prepared.

(1) N-(4-Chlorobenzyl)-4-mercaptothieno[2,3-b]pyridine-5-carboxamide;
(2) N-(4-Chlorobenzyl)-4-mercapto-2-iodothieno[2,3-b]pyridine-5-carboxamide;
(3) N-(4-Chlorobenzyl)-4-mercapto-2-(4-morpholinylsulfonyl)thieno[2,3-b]-pyridine-5-carboxamide;
(4) 2-Bromo-N-(4-chlorobenzyl)-4-mercaptothieno[2,3-b]pyridine-5-carboxamide;
(5) N-(4-Chlorobenzyl)-4-mercapto-2-(3-hydroxy-1-propynyl)thieno[2,3-b]-pyridine-5-carboxamide;
(6) N-(4-Chlorobenzyl)-4-mercapto-2-(3-methoxy-1-propynyl)thieno[2,3-b]-pyridine-5-carboxamide;
(7) N-(4-Chlorobenzyl)-4-mercapto-2-(4-hydroxy-1-butynyl)thieno[2,3-b]-pyridine-5-carboxamide;
(8) N-(4-Chlorobenzyl)-4-mercapto-2-(3-hydroxypropyl)thieno[2,3-b]pyridine-5-carboxamide;
(9) N-(4-Chlorobenzyl)-2-cyano-4-mercaptothieno[2,3-b]pyridine-5-carboxamide;
(10) Dimethyl 2-[3-(5-{[(4-chlorobenzyl)amino]carbonyl}-4-mercaptothieno[2,3-b]pyridin-2-yl)-2-propynyl]malonate;
(11) 2-Bromo-N-(4-chlorobenzyl)-7-ethyl-4-thioxo-4,7-dihydrothieno[2,3-b]-pyridine-5-carboxamide;
(12) N-(4-Chlorobenzyl)-7-ethyl-4-thioxo-4,7-dihydrothieno[2,3-b]pyridine-5-carboxamide;
(13) N-(4-Chlorobenzyl)-7-ethyl-2-iodo-4-thioxo-4,7-dihydrothieno[2,3-b]-pyridine-5-carboxamide;
(14) N-(4-Chlorobenzyl)-7-ethyl-2-(3-hydroxy-1-propynyl)-4-thioxo-4,7-dihydrothieno[2,3-b]pyridine-5-carboxamide;
(15) N-(4-Chlorobenzyl)-7-ethyl-2-(4-hydroxy-1-butynyl)-4-thioxo-4,7-dihydrothieno[2,3-b]pyridine-5-carboxamide;
(16) N-(4-Chlorobenzyl)-7-ethyl-2-(3-hydroxypropyl)-4-thioxo-4,7-dihydrothieno[2,3-b]pyridine-5-carboxamide;
(17) N-(4-Chlorobenzyl)-7-(2-hydroxyethyl)-2-(3-hydroxy-1-propynyl)-4-thioxo-4,7-dihydrothieno[2,3-b]pyridine-5-carboxamide;
(18) N-(4-Chlorobenzyl)-7-[2-(diethylamino)ethyl]-2-(3-hydroxy-1-propynyl)-4-thioxo-4,7-dihydrothieno[2,3-b]pyridine-5-carboxamide;
(19) 2-[5-{[(4-Chlorobenzyl)amino]carbonyl}-2-(3-hydroxy-1-propynyl)-4-thioxothieno[2,3-b]pyridin-7(4H)-yl]acetic acid;
(20) N-(4-Chlorobenzyl)-7-ethyl-2-(4-hydroxybutyl)-4-thioxo-4,7-dihydrothieno[2,3-b]pyridine-5-carboxamide;
(21) N-(4-Chlorobenzyl)-7-(2-hydroxyethyl)-2-(3-hydroxypropyl)-4-thioxo-4,7-dihydrothieno[2,3-b]pyridine-5-carboxamide;
(22) N-(4-Chlorobenzyl)-7-[2-(diethylamino)ethyl]-2-(3-hydroxypropyl)-4-thioxo-4,7-dihydrothieno[2,3-b]pyridine-5-carboxamide;
(23) N-(4-Chlorobenzyl)-2-iodo-7-methyl-4-thioxo-4,7-dihydrothieno[2,3-b]-pyridine-5-carboxamide;
(24) N-(4-Chlorobenzyl)-2-(3-hydroxy-1-propynyl)-7-methyl-4-thioxo-4,7-dihydrothieno[2,3-b]pyridine-5-carboxamide;
(25) N-(4-Chlorobenzyl)-2-(3-hydroxypropyl)-7-methyl-4-thioxo-4,7-dihydrothieno[2,3-b]pyridine-5-carboxamide;
(26) N-(4-Chlorobenzyl)-2-iodo-7-isopropyl-4-thioxo-4,7-dihydrothieno[2,3-b]-pyridine-5-carboxamide;
(27) N-(4-Chlorobenzyl)-2-(3-hydroxy-1-propynyl)-7-isopropyl-4-thioxo-4,7-dihydrothieno[2,3-b]pyridine-5-carboxamide;
(28) N-(4-Chlorobenzyl)-2-(3-hydroxypropyl)-7-isopropyl-4-thioxo-4,7-dihydrothieno[2,3-b]pyridine-5-carboxamide;
(29) 4-{[3-(5-{[(4-Chlorobenzyl)amino]carbonyl}-7-ethyl-4-thioxo-4,7-dihydrothieno[2,3-b]pyridin-2-yl)-2-propynyl]oxy}-4-oxobutanoic acid;
(30) 3-(5-{[(4-Chlorobenzyl)amino]carbonyl}-7-ethyl-4-thioxo-4,7-dihydrothieno[2,3-b]pyridin-2-yl)-2-propynyl 2-(4-morpholinyl)acetate;
(31) 3-(5-{[(4-Chlorobenzyl)amino]carbonyl}-7-ethyl-4-thioxo-4,7-dihydrothieno[2,3-b]pyridin-2-yl)-2-propynyl 2-amino-3-methylbutanoate;
(32) 3-(5-{[(4-Chlorobenzyl)amino]carbonyl}-7-ethyl-4-thioxo-4,7-dihydrothieno[2,3-b]pyridin-2-yl)-2-propynyl 3-(4-morpholinylmethyl)benzoate;
(33) N-(4-chlorobenzyl)-2-(hydroxymethy)-7-methyl-4-thioxo-4,7-dihydrothienol[2,3-b]pyridine-5-carboxamide;
(34) N-(4-chlorobenzyl)-7-methyl-2-(4-morpholinylmethyl)-4-thioxo-4,7-dihydrothienol[2,3-b]pyridine-5-carboxamide;
(35) N-(4-chlorobenzyl)-7-methyl-2-(4-morpholinylmethyl)-4-thioxo-4,7-dihydrothieno[2,3-b]pyridine-5-carboxamide;
(36) N-(4-chlorobenzyl)-7-methyl-4-thioxo-2-(4-thiomorpholinylmethyl)-4,7-dihydrothieno[2,3-b]pyridine-5-carboxamide;
(37) N-(4-chlorobenzyl)-2-(((2-hydroxy-2-(4-hydroxyphenyl)ethyl)-(methyl)amino)methyl)-7-methyl-4-thioxo-4,7-dihydrothieno[2,3-b]pyridine-5-carboxamide;
(38) N-(4-chlorobenzyl)-2-(((2-hydroxy-2-phenylethyl)(methyl)-amino)methyl)-7-methyl-4-thioxo-4,7-dihydrothieno[2,3-b]pyridine-5-carboxamide;
(39) N-(4-chlorobenzyl)-4-mercapto-2-(4-morpholinylmethyl)thieno[2,3-b]pyridine-5-carboxamide;

(40) N-(4-Chlorobenzyl)-7-ethyl-2-(4-morpholinylmethyl)-4-thioxo-4,7-dihydrothieno[2,3-b]pyridine-5-carboxamide;

(41) N-(4-Chlorobenzyl)-2-(4-morpholinylmethyl)-4-thioxo-7-propyl-4,7-dihydrothieno[2,3-b]pyridine-5-carboxamide;

(42) N-(4-Chlorobenzyl)-7-isopropyl-2-(4-morpholinylmethyl)-4-thioxo-4,7-dihydrothieno[2,3-b]pyridine-5-carboxarnide;

(43) N-(4-Fluorobenzyl)-7-methyl-2-(4-morpholinytmethyl)-4-thioxo-4,7-dihydrothieno[2,3-b]pyridine-5-carboxamide;

(44) N-(4-bromobenzyl)-7-methyl-2-(4-morpholinylmethyl)-4-thioxo-4,7-dihydrothieno[2,3-b]pyridine-5-carboxamide;

(45) N-(4-chlorobenzyl)-7-methyl-2-(4-morpholinylcarbonyl)-4-thioxo-4,7-dihydrothieno[2,3-b]pyridine-5-carboxamide;

(46) 7-Benzyl-N-(4-chlorobenzyl)-2-(4-morpholinylmethyl)-4-thioxo-4,7-dihydrothieno[2,3-b]pyridine-5-carboxamide;

(47) N-(4-Chlorobenzyl)-7-(3-fluorobenzyl)-2-(4-morpholinylmethyl)-4-thioxo-4,7-dihydrothieno[2,3-b]pyridine-5-carboxamide;

(48) N-(4-Chlorobenzyl)-2-(4-morpholinytmethyl)-4-thioxo-7-(3-phenylpropyl)-4,7-dihydrothieno[2,3-b]pyridine-5-carboxamide;

(49) N-(4-Chlorobenzyl)-2-(4-morpholinylmethyl)-4-thioxo-7-(tetrahydro-2-furanylmethyl)-4,7-dihydrothieno[2,3-b]pyridine-5-carboxamide;

(50) N-(4-Chlorobenzyl)-2-(4-morpholinylmethyl)-4-thioxo-7-[2-(1-pyrrolidinyl)ethyl]-4,7-dihydrothieno[2,3-b]pyridine-5-carboxamide;

(51) N-(4-Chlorobenzyl)-2-(4-morpholinylmethyl)-4-thioxo-7-(3-pyridinylmethyl)-4,7-dihydrothieno[2,3-b]pyridine-5-carboxamide;

(52) N-(4-Chlorobenzyl)-2-(4-morpholinylmethyl)-4-thioxo-7-(4-pyridinylmethyl)-4,7-dihydrothieno[2,3-b]pyridine-5-carboxamide;

(53) Methyl-5-{[4-chlorobenzyl)amino]carbonyl}-4-mercaptothienol[2,3-b]pyridine-2-carboxylate;

(54) N-(4-Chlorobenzyl)-4-mercapto-2-(hydroxymethyl)thieno[2,3-b]pyridine-5-carboxamide; and

(55) N-(4-chlorobenzyl)-4-mercapto-2-(4-morpholinylcarbonyl)thieno[2,3-b]pyridine-5-carboxamide; or a pharmaceutically acceptable salt thereof.

A specific compound of the invention is, (1) N-(4-Chlorobenzyl)-7-ethyl-2-(3-hydroxy-1-propynyl)-4-thioxo-4,7-dihydro-thieno[2,3-b]pyridine-5-carboxamide;

(2) N-(4-Chlorobenzyl)-7-ethyl-2-(4-hydroxy-1-butynyl)-4-thioxo-4,7-dihydro-thieno[2,3-b]pyridine-5-carboxamide;

(3) N-(4-Chlorobenzyl)-7-ethyl-2-(3-hydroxypropyl)-4-thioxo-4,7-dihydro-thieno[2,3-b]pyridine-5-carboxamide;

(4) N-(4-Chlorobenzyl)-7-(2-hydroxyethyl)-2-(3-hydroxy-1-propynyl)-4-thioxo-4,7-dihydrothieno[2,3-b]pyridine-5-carboxamide;

(5) N-(4-Chlorobenzyl)-7-[2-(diethylamino)ethyl]-2-(3-hydroxy-1-propynyl)-4-thioxo-4,7-dihydrothieno[2,3-b]pyridine-5-carboxamide;

(6) N-(4-Chlorobenzyl)-7-ethyl-2-(4-hydroxybutyl)-4-thioxo-4,7-dihydro-thieno[2,3-b]pyridine-5-carboxamide;

(7) N-(4-Chlorobenzyl)-7-(2-hydroxyethyl)-2-(3-hydroxypropyl)-4-thioxo-4,7-dihydrothieno[2,3-b]pyridine-5-carboxamide;

(8) N-(4-Chlorobenzyl)-7-[2-(diethylamino)ethyl]-2-(3-hydroxypropyl)-4-thioxo-4,7-dihydrothieno[2,3-b]pyridine-5-carboxamide;

(9) N-(4-Chlorobenzyl)-2-iodo-7-methyl-4-thioxo-4,7-dihydrothieno[2,3-b]-pyridine-5-carboxamide;

(10) N-(4-Chlorobenzyl)-2-(3-hydroxy-1-propynyl)-7-methyl-4-thioxo-4,7-dihydrothieno[2,3-b]pyridine-5-carboxamide;

(11) N-(4-Chlorobenzyl)-2-(3-hydroxypropyl)-7-methyl-4-thioxo-4,7-dihydro-thieno[2,3-b]pyridine-5-carboxamide;

(12) N-(4-Chlorobenzyl)-2-iodo-7-isopropyl-4-thioxo-4,7-dihydrothieno[2,3-b]-pyridine-5-carboxamide;

(13) N-(4-Chlorobenzyl)-2-(3-hydroxy-1-propynyl)-7-isopropyl-4-thioxo-4,7-dihydrothieno[2,3-b]pyridine-5-carboxamide;

(14) N-(4-Chlorobenzyl)-2-(3-hydroxypropyl)-7-isopropyl-4-thioxo-4,7-dihydro-thieno[2,3-b]pyridine-5-carboxamide;

(15) 4-{[3-(5-{[(4-Chlorobenzyl)amino]carbonyl}-7-ethyl-4-thioxo-4,7-dihydro-thieno[2,3-b]pyridin-2-yl)-2-propynyl]oxy}-4-oxobutanoic acid;

(16) 3-(5-{[(4-Chlorobenzyl)amino]carbonyl}-7-ethyl-4-thioxo-4,7-dihydro-thieno[2,3-b]pyridin-2-yl)-2-propynyl 2-(4-morpholinyl)acetate;

(17) 3-(5-{[(4-Chlorobenzyl)amino]carbonyl}-7-ethyl-4-thioxo-4,7-dihydro-thieno[2,3-b]pyridin-2-yl)-2-propynyl 2-amino-3-methylbutanoate;

(18) 3-(5-{[(4-Chlorobenzyl)amino]carbonyl}-7-ethyl-4-thioxo-4,7-dihydro-thieno[2,3-b]pyridin-2-yl)-2-propynyl 3-(4-morpholinylmethyl)benzoate;

(19) N-(4-chlorobenzyl)-7-methyl-2-(4-morpholinylmethyl)-4-thioxo-4,7-dihydrothienol[2,3-b]pyridine-5-carboxamide;

(20) N-(4-chlorobenzyl)-7-methyl-2-(4-morpholinylmethyl)-4-thioxo-4,7-dihydrothieno[2,3-b]pyridine-5-carboxamide;

(21) N-(4-chlorobenzyl)-7-methyl-4-thioxo-2-(4-thiomorpholinylmethyl)-4,7-dihydrothieno[2,3-b]pyridine-5-carboxamide;

(22) N-(4-chlorobenzyl)-2-(((2-hydroxy-2-(4-hydroxyphenyl)ethyl)-(methyl)amino)methyl)-7-methyl-4-thioxo-4,7-dihydrothieno[2,3-b]pyridine-5-carboxamide;

(23) N-(4-chlorobenzyl)-2-(((2-hydroxy-2-phenylethyl)(methyl)arnino)methyl)-7-methyl-4-thioxo-4,7-dihydrothieno[2,3-b]pyridine-5-carboxamide;

(24) N-(4-Chlorobenzyl)-7-ethyl-2-(4-morpholinylmethyl)-4-thioxo-4,7-dihydrothieno[2,3-b]pyridine-5-carboxamide;

(25) N-(4-Chlorobenzyl)-2-(4-morpholinylmethyl)-4-thioxo-7-propyl-4,7-dihydrothieno[2,3-b]pyridine-5-carboxamide;

(26) N-(4-Chlorobenzyl)-7-isopropyl-2-(4-morpholinylmethyl)-4-thioxo-4,7-dihydrothieno[2,3-b]pyridine-5-carboxamide;

(27) N-(4-Fluorobenzyl)-7-methyl-2-(4-morpholinylmethyl)-4-thioxo-4,7-dihydrothieno[2,3-b]pyridine-5-carboxamide;

(28) N-(4-bromobenzyl)-7-methyl-2-(4-morpholinylmethyl)-4-thioxo-4,7-dihydrothieno[2,3-b]pyridine-5-carboxamide;

(29) 7-Benzyl-N-(4-chlorobenzyl)-2-(4-morpholinylmethyl)-4-thioxo-4,7-dihydrothieno[2,3-b]pyridine-5-carboxamide;

(30) N-(4-Chlorobenzyl)-7-(3-fluorobenzyl)-2-(4-morpholinylmethyl)-4-thioxo-4,7-dihydrothieno[2,3-b]pyridine-5-carboxamide;

(31) N-(4-Chlorobenzyl)-2-(4-morpholinylmethyl)-4-thioxo-7-(3-phenylpropyl)-4,7-dihydrothieno[2,3-b]pyridine-5-carboxamide;

(32) N-(4-Chlorobenzyl)-2-(4-morpholinylmethyl)-4-thioxo-7-(tetrahydro-2-furanylmethyl)-4,7-dihydrothieno[2,3-b]pyridine-5-carboxamide;

(33) N-(4-Chlorobenzyl)-2-(4-morpholinylmethyl)-4-thioxo-7-[2-(1-pyrrolidinyl)ethyl]-4,7-dihydrothieno[2,3-b]pyridine-5-carboxamide;

(34) N-(4-Chlorobenzyl)-2-(4-morpholinylmethyl)-4-thioxo-7-(3-pyridinylmethyl)-4,7-dihydrothieno[2,3-b]pyridine-5-carboxamide; or

(35) N-(4-Chlorobenzyl)-2-(4-morpholinylmethyl)-4-thioxo-7-(4-pyridinylmethyl)-4,7-dihydrothieno[2,3-b]pyridine-5-carboxamide; or a pharmaceutically acceptable salt thereof.

Another specific compound of the invention is, (1) N-(4-Chlorobenzyl)-7-ethyl-2-(3-hydroxy-1-propynyl)-4-thioxo-4,7-dihydro-thieno[2,3-b]pyridine-5-carboxamide;

(2) N-(4-Chlorobenzyl)-7-ethyl-2-(4-hydroxy-1-butynyl)-4-thioxo-4,7-dihydro-thieno[2,3-b]pyridine-5-carboxamide;

(3) N-(4-Chlorobenzyl)-7-ethyl-2-(3-hydroxypropyl)-4-thioxo-4,7-dihydro-thieno[2,3-b]pyridine-5-carboxamide;

(4) N-(4-Chlorobenzyl)-7-(2-hydroxyethyl)-2-(3-hydroxy-1-propynyl)-4-thioxo-4,7-dihydrothieno[2,3-b]pyridine-5-carboxamide;

(5) N-(4-Chlorobenzyl)-7-[2-(diethylamino)ethyl]-2-(3-hydroxy-1-propynyl)-4-thioxo-4,7-dihydrothieno[2,3-b]pyridine-5-carboxamide;

(6) N-(4-Chlorobenzyl)-7-ethyl-2-(4-hydroxybutyl)-4-thioxo-4,7-dihydro-thieno[2,3-b]pyridine-5-carboxamide;

(7) N-(4-Chlorobenzyl)-7-(2-hydroxyethyl)-2-(3-hydroxypropyl)-4-thioxo-4,7-dihydrothieno[2,3-b]pyridine-5-carboxamide;

(8) N-(4-Chlorobenzyl)-7-[2-(diethylamino)ethyl]-2-(3-hydroxypropyl)-4-thioxo-4,7-dihydrothieno[2,3-b]pyridine-5-carboxamide;

(9) N-(4-Chlorobenzyl)-2-iodo-7-methyl-4-thioxo-4,7-dihydrothieno[2,3-b]-pyridine-5-carboxamide;

(10) N-(4-Chlorobenzyl)-2-(3-hydroxy-1-propynyl)-7-methyl-4-thioxo-4,7-dihydrothieno[2,3-b]pyridine-5-carboxamide;

(11) N-(4-Chlorobenzyl)-2-(3-hydroxypropyl)-7-methyl-4-thioxo-4,7-dihydro-thieno[2,3-b]pyridine-5-carboxamide;

(12) N-(4-Chlorobenzyl)-2-iodo-7-isopropyl-4-thioxo-4,7-dihydrothieno[2,3-b]-pyridine-5-carboxamide;

(13) N-(4-Chlorobenzyl)-2-(3-hydroxy-1-propynyl)-7-isopropyl-4-thioxo-4,7-dihydro-thieno[2,3-b]pyridine-5-carboxamide;

(14) N-(4-Chlorobenzyl)-2-(3-hydroxypropyl)-7-isopropyl-4-thioxo-4,7-dihydro-thieno[2,3-b]pyridine-5-carboxamide;

(15) N-(4-chlorobenzyl)-7-methyl-2-(4-morpholinylmethyl)-4-thioxo-4,7-dihydrothieno[2,3-b]pyridine-5-carboxamide;

(16) N-(4-chlorobenzyl)-7-methyl-2-(4-morpholinylmethyl)-4-thioxo-4,7-dihydrothieno[2,3-b]pyridine-5-carboxamide;

(17) N-(4-chlorobenzyl)-7-methyl-4-thioxo-2-(4-thiomorpholinylmethyl)-4,7-dihydrothieno[2,3-b]pyridine-5-carboxamide;

(18) N-(4-chlorobenzyl)-2-(((2-hydroxy-2-(4-hydroxyphenyl)ethyl)-(methyl)amino)methyl)-7-methyl-4-thioxo-4,7-dihydrothieno[2,3-b]pyridine-5-carboxamide;

(19) N-(4-chlorobenzyl)-2-(((2-hydroxy-2-phenylethyl)(methyl)-amino)methyl)-7-methyl-4-thioxo-4,7-dihydrothieno[2,3-b]pyridine-5-carboxamide;

(20) N-(4-Chlorobenzyl)-7-ethyl-2-(4-morpholinylmethyl)-4-thioxo-4,7-dihydrothieno[2,3-b]pyridine-5-carboxamide;

(21) N-(4-Chlorobenzyl)-2-(4-morpholinylmethyl)-4-thioxo-7-propyl-4,7-dihydrothieno[2,3-b]pyridine-5-carboxamide;

(22) N-(4-Chlorobenzyl)-7-isopropyl-2-(4-morpholinylmethyl)-4-thioxo-4,7-dihydrothieno[2,3-b]pyridine-5-carboxamide;

(23) N-(4-Fluorobenzyl)-7-methyl-2-(4-morpholinylmethyl)-4-thioxo-4,7-dihydrothieno[2,3-b]pyridine-5-carboxamide;

(24) N-(4-bromobenzyl)-7-methyl-2-(4-morpholinylmethyl)-4-thioxo-4,7-dihydrothieno[2,3-b]pyridine-5-carboxamide;

(25) 7-Benzyl-N-(4-chlorobenzyl)-2-(4-morpholinylmethyl)-4-thioxo-4,7-dihydrothieno[2,3-b]pyridine-5-carboxamide;

(26) N-(4-Chlorobenzyl)-7-(3-fluorobenzyl)-2-(4-morpholinylmethyl)-4-thioxo-4,7-dihydrothieno[2,3-b]pyridine-5-carboxamide;

(27) N-(4-Chlorobenzyl)-2-(4-morpholinylmethyl)-4-thioxo-7-(tetrahydro-2-furanylmethyl)-4,7-dihydrothieno[2,3-b]pyridine-5-carboxamide;

(28) N-(4-Chlorobenzyl)-2-(4-morpholinylmethyl)-4-thioxo-7-[2-(1-pyrrolidinyl)ethyl]-4,7-dihydrothieno[2,3-b]pyridine-5-carboxamide;

(29) N-(4-Chlorobenzyl)-2-(4-morpholinylmethyl)-4-thioxo-7-(3-pyridinylmethyl)-4,7-dihydrothieno[2,3-b]pyridine-5-carboxamide; or

(30) N-(4-Chlorobenzyl)-2-(4-morpholinylmethyl)-4-thioxo-7-(4-pyridinylmethyl)-4,7-dihydrothieno[2,3-b]pyridine-5-carboxamide; or a pharmaceutically acceptable salt thereof.

A more specific compound of the invention is (1) N-(4-Chlorobenzyl)-7-[2-(diethylamino)ethyl]-2-(3-hydroxypropyl)-4-thioxo-4,7-dihydrothieno[2,3-b]pyridine-5-carboxamide;

(2) N-(4-Chlorobenzyl)-2-(3-hydroxy-1-propynyl)-7-methyl-4-thioxo-4,7-dihydro-thieno[2,3-b]pyridine-5-carboxamide;

(3) N-(4-Chlorobenzyl)-2-(3-hydroxypropyl)-7-methyl-4-thioxo-4,7-dihydro-thieno[2,3-b]pyridine-5-carboxamide;

(4) N-(4-chlorobenzyl)-7-methyl-2-(4-morpholinylmethyl)-4-thioxo-4,7-dihydrothieno[2,3-b]pyridine-5-carboxamide;

(5) N-(4-chlorobenzyl)-2-(((2-hydroxy-2-(4-hydroxyphenyl)ethyl)(methyl)-amino)methyl)-7-methyl-4-thioxo-4,7-dihydrothieno[2,3-b]pyridine-5-carboxamide;

(6) N-(4-chlorobenzyl)-2-(((2-hydroxy-2-phenylethyl)(methyl)-amino)methyl)-7-methyl-4-thioxo-4,7-dihydrothieno[2,3-b]pyridine-5-carboxamide;

(7) N-(4-Chlorobenzyl)-7-ethyl-2-(4-morpholinylmethyl)-4-thioxo-4,7-dihydrothieno[2,3-b]pyridine-5-carboxamide; or (8) N-(4-Chlorobenzyl)-2-(4-morpholinylmethyl)-4-thioxo-7-propyl-4,7-dihydrothieno[2,3-b]pyridine-5-carboxamide; or a pharmaceutically acceptable salt thereof.

Another more specific compound of the invention is N-(4-chlorobenzyl)-7-methyl-2-(4-morpholinylmethyl)-4-thioxo-4,7-dihydrothieno[2,3-b]pyridine-5-carboxamide or a pharmaceutically acceptable salt thereof.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

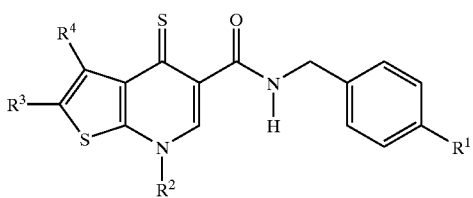

or a pharmnaceutically acceptable salt thereof wherein, $R^1$ is
(a) Cl,
(b) Br,
(c) CN, (d) $NO_2$, or
(e) F;

$R^2$ is
(a) H,
(b) $R^5$,
(c) $NR^7R^8$,
(d) $SO_2R^9$, or
(e) $OR^5$;

$R^3$ is
(a) H,
(b) halo,
(c) aryl,
(d) $S(O)_mR^6$,
(e) $(C=O)R^6$,
(f) $(C=O)OR^9$,
(g) cyano,
(h) het, wherein said het is bound via a carbon atom,
(i) $OR^{10}$,
(j) Ohet,
(k) $NR^7R^8$
(l) $SR^{10}$,
(m) Shet,
(n) $NHCOR^{12}$,
(o) $NHSO_2R^{12}$, or
(p) $C_{1-7}$alkyl which may be partially unsaturated and optionally substituted by one or more substituents of the group $R^{11}$, $OR^{13}$, $SR^{10}$, $SR^{13}$, $NR^7R^8$, halo, $(C=O)C_{1-7}$alkyl, or $SO_mR^9$;

$R^4$ is
(a) H,
(b) halo,
(c) $C_{1-4}$alkyl, or
(d) $R^4$ together with $R^3$ form a carbocyclic or het, either of which may be optionally substituted by $NR^7R^8$, by $C_{1-7}$alkyl which may be optionally substituted by $OR^{14}$, or by het, wherein said het is bound via a carbon atom;

$R^5$ is
(a) $(CH_2CH_2O)_iR^{10}$,
(b) het, wherein said het is bound via a carbon atom,
(c) aryl,
(d) $C_{1-7}$alkyl which may be partially unsaturated and is optionally substituted by one or more substituents selected from a group consisting of $NR^7R^8$, $R^{11}$, $SO_mR^9$, and $OC_{2-4}$alkyl which may be further substituted by het, $OR^{10}$, or $NR^7R^8$, or
(e) $C_{3-8}$cycloalkyl which may be partially unsaturated and optionally substituted by one or more substituents selected from a group consisting of $R^{11}$, $NR^7R^8$, $SO_mR^9$, and $C_{1-7}$alkyl optionally substituted by $R^{11}$, $NR^7R^8$, or $SO_mR^9$;

$R^6$ is
(a) $C_{1-7}$alkyl,
(b) $NR^7R^8$,
(c) aryl, or
(d) het, wherein said het is bound via a carbon atom;

$R^7$ and $R^8$ are independently
(a) H,
(b) aryl,
(c) $C_{1-7}$alkyl which may be partially unsaturated and is optionally substituted by one or more substituents selected from a group consisting of $NR^{10}R^{10}$, $R^{11}$, $SO_mR^9$, $CONR^{10}R^{10}$, or halo, or,
(d) $R^7$ and $R^8$ together with the nitrogen to which they are attached form a het;

$R^9$ is
(a) aryl,
(b) het,
(c) $C_{3-8}$cycloalkyl, or
(d) $C_{1-7}$alkyl which may be partially unsaturated and is optionally substituted by one or more substituents selected from a group consisting of $NR^{10}R^{10}$, $R^{11}$, SH, $CONR^{10}R^{10}$, or halo;

$R^{10}$ is
(a) H, or
(b) $C_{1-7}$alkyl optionally substituted by OH;

$R^{11}$ is
(a) $OR^{10}$,
(b) Ohet,
(c) Oaryl,
(d) $CO_2R^{10}$,
(e) het,
(f) aryl, or
(g) CN;

$R^{12}$ is
(a) H,
(b) het,
(c) aryl,
(d) $C_{3-8}$cycloalkyl, or
(e) $C_{1-7}$alkyl optionally substituted by $NR^7R^8$ or $R^{11}$;

23

$R^{13}$ is
- (a) $(P=O)(OR^{14})_2$,
- (b) $CO(CH_2)_n CON(CH_3)—(CH_2)_n SO_3^- M^+$,
- (c) an amino acid,
- (d) $C(=O)$aryl, or
- (e) $C(=O)C_{1-7}$alkyl optionally substituted by $NR^7 R^8$, aryl, het, $CO_2 H$, or $O(CH_2)_n CO_2 R^{14}$);

$R^{14}$ is
- (a) H, or
- (b) $C_{1-7}$alkyl;

each i is independently 2, 3, or 4;
each n is independently 1, 2, 3, 4 or 5;
each m is independently 0, 1, or 2; and
M is sodium, potassium, or lithium;
wherein any aryl is optionally substituted with one or more substituents selected from the group consisting of halo, OH, cyano, $CO_2 R^{14}$, $CF_3$, $C_{1-6}$alkoxy, and $C_{1-6}$ alkyl which maybe further substituted by one to three $SR^{14}$, $NR^{14} R^{14}$, $OR^{14}$, het, and $CO_2 R^{14}$; and
wherein any het is optionally substituted with one or more substituents selected from the group consisting of halo, OH, cyano, phenyl, $CO_2 R^{14}$, $CF_3$, $C_{1-6}$alkoxy, oxo, oxime, and $C_{1-6}$alkyl which maybe further substituted by one to three $SR^{14}$, $NR^{14} R^{14}$, $OR^{14}$, and $CO_2 R^{14}$.

2. The compound of claim 1 wherein $R^1$ is F, Cl or Br.
3. The compound of claim 1 wherein $R^1$ is Cl.
4. The compound of claim 1 wherein $R^2$ is H.
5. The compound of claim 1 wherein $R^2$ is $R^5$, $NR^7 R^8$, $SO_2 R^9$, or $OR^9$.
6. The compound of claim 5 wherein $R^2$ is $R^5$ and $R^5$ is $C_{1-7}$alkyl which may be partially unsaturated and is optionally substituted by one or more substituents selected from a group consisting of $NR^7 R^8$, $R^{11}$, $SO_m R^9$, and $OC_{2-4}$alkyl, which may be further substituted by het, $OR^{10}$, or $NR^7 R^8$.
7. The compound of claim 5 wherein $R^2$ is $R^5$ and $R^5$ is $C_{1-7}$alkyl, which may be partially unsaturated and is optionally substituted by one or more aryl or het.
8. The compound of claim 7 wherein $R^5$ is $C_{1-7}$alkyl.
9. The compound of claim 1 wherein $R^2$ is methyl, ethyl, propyl, isopropyl, butyl, tert-butyl, carboxymethyl, ($C_{1-7}$alkoxy)carbonylmethyl, 2-hydroxyethyl, 2-(2-methoxyethoxy)ethyl, 3-(2-tetrahydropyranyloxy)propyl, 2-morpholinoethyl, 2-(diethylamino)ethyl, 2-(dimethylamino)ethyl, 2-piperidinoethyl, 3-piperidinopropyl, 2-(1-methylpyrrolidin-2-yl)ethyl, 2-(diisopropylamino)ethyl, 2-pyrrolidin-1-ylethyl, 3-(dimethylamino)propyl, benzyl, 3-fluorobenzyl, 3-phenylpropyl, 2-tetrahydrofuranylmethyl, 2-pyrrolidinoethyl, 3-pyridylmethyl, or vinyl.
10. The compound of claim 1 wherein $R^2$ is methyl, ethyl, isopropyl, 2-hydroxyethyl, 2-(diethylamino)ethyl, or 2-(dimethylamino)ethyl.
11. The compound of claim 1 wherein $R^3$ is H, halo, $S(O)_m R^6$, $(C=O)R^6$, $(C=O)OR^9$, cyano, or $C_{1-7}$alkyl, which may be partially unsaturated and optionally substituted by one or more substituents of the group $R^{11}$, $OR^{13}$ $SR^{10}$, $SR^{13}$, $NR^7 R^8$, halo, $(C=O)C_{1-7}$alkyl, and $SO_m R^9$.
12. The compound of claim 1 wherein $R^3$ is $C_{1-7}$alkyl which may be partially unsaturated and optionally substituted by one or more substituents of the group $R^{11}$, $OR^{13}$, $SR^{10}$, $SR^{13}$, $NR^7 R^8$, halo, $(C=O)C_{1-7}$alkyl, and $SO_m R^9$.
13. The compound of claim 1 wherein $R^3$ is $C_{1-7}$alkyl which may be partially unsaturated and is substituted by one or more substituents of the group $R^{11}$, $OR^{13}$, $SR^{10}$, $SR^{13}$, $NR^7 R^8$, halo, $(C=O)C_{1-7}$alkyl, and $SO_m R^9$.
14. The compound of claim 1 wherein $R^3$ is $C_{1-7}$alkyl which may be partially unsaturated and is substituted by one or more substituents of the group $OR^{10}$, het and $NR^7 R^8$.

24

15. The compound of claim 1 wherein $R^3$ is bromo, iodo, 3-hydroxy-1-propynyl, 3-methoxy-1-propynyl, 4-hydroxy-1-butynyl, 3-hydroxypropyl, cyano, 4,4-di(methoxycarbonyl)-1-butynyl, 4-hydroxybutyl, 3-(3-carboxypropanoyloxy)-1-propynyl, 3-(morpholinoacetoxy)-1-propynyl, 3-(2-amino-3-methylbutanoyloxy)-1-propynyl, or thiomorpholinomethyl, N-[2-(4-hydroxyphenyl)-2-hydroxyethyl]-N-(methyl)aminomethyl, morpholinocarbonyl, 3-[3-(morpholinomethyl)benzoyloxy]-1-propynyl.
16. The compound of claim 1 wherein $R^3$ is iodo, 3-hydroxy-1-propynyl, 4-hydroxy-1-butynyl, 3-hydroxypropyl, morpholimomethyl, N-[2-(4-hydroxyphenyl)-2-hydroxyethyl]-N-(methyl)aminomethyl or 4-hydroxybutyl.
17. The compound of claim 1 wherein $R^3$ is 3-hydroxy-1-propynyl, morpholimomethyl, N-[2-(4-hydroxyphenyl)-2-hydroxyethyl]-N-(methyl)aminomethyl or 3-hydroxypropyl.
18. The compound of claim 1 which is:
(1) N-(4-Chlorobenzyl)-4-mercaptothieno[2,3-b]pyridine-5-carboxamide;
(2) N-(4-Chlorobenzyl)-4-mercapto-2-iodothieno[2,3-b]pyridine-5-carboxamide;
(3) N-(4-Chlorobenzyl)-4-mercapto-2-(4-morpholinylsulfonyl)thieno[2,3-b]-pyridine-5-carboxamide;
(4) 2-Bromo-N-(4-chlorobenzyl)-4-mercaptothieno[2,3-b]pyridine-5-carboxamide;
(5) N-(4-Chlorobenzyl)-4-mercapto-2-(3-hydroxy-1-propynyl)thieno[2,3-b]-pyridine-5-carboxamide;
(6) N-(4-Chlorobenzyl)-4-mercapto-2-(3-methoxy-1-propynyl)thieno[2,3-b]-pyridine-5-carboxamide;
(7) N-(4-Chlorobenzyl)-4-mercapto-2-(4-hydroxy-1-butynyl)thieno[2,3-b]-pyridine-5-carboxamide;
(8) N-(4-Chlorobenzyl)-4-mercapto-2-(3-hydroxypropyl)thieno[2,3-b]pyridine-5-carboxamide;
(9) N-(4-Chlorobenzyl)-2-cyano-4-mercaptothieno[2,3-b]pyridine-5-carboxamide;
(10) Dimethyl 2-[3-(5-({[(4-chlorobenzyl)amino]carbonyl }-4-mercaptothieno[2,3-b]pyridin-2-yl)-2-propynyl]malonate;
(11) 2-Bromo-N-(4-chlorobenzyl)-7-ethyl-4-thioxo-4,7-dihydrothieno[2,3-b]-pyridine-5-carboxamide;
(12) N-(4-Chlorobenzyl)-7-ethyl-4-thioxo-4,7-dihydrothieno[2,3-b]pyridine-5-carboxamide;
(13) N-(4-Chlorobenzyl)-7-ethyl-2-iodo-4-thioxo-4,7-dihydrothieno[2,3-b]-pyridine-5-carboxamide;
(14) N-(4-Chlorobenzyl)-7-ethyl-2-(3-hydroxy-1-propynyl)-4-thioxo-4,7-dihydrothieno[2,3-b]pyridine-5-carboxamide;
(15) N-(4-Chlorobenzyl)-7-ethyl-2-(4-hydroxy-butynyl)-4-thioxo-4,7-dihydrothieno[2,3-b]pyridine-5-carboxamide;
(16) N-(4-Chlorobenzyl)-7-ethyl-2-(3-hydroxypropyl)-4-thioxo-4,7-dihydrothieno[2,3-b]pyridine-5-carboxamide;
(17) N-(4-Chlorobenzyl)-7-(2-hydroxyethyl)-2-(3-hydroxy-1-propynyl)-4-thioxo-4,7-dihydrothieno[2,3-b]pyridine-5-carboxamide;
(18) N-(4-Chlorobenzyl)-7-[2-(diethylamino)ethyl]-2-(3-hydroxy-1-propynyl)-4-thioxo-4,7-dihydrothieno[2,3-b]pyridine-5-carboxamide;
(19) 2-[5-{[(4-Chlorobenzyl)amino]carbonyl }-2-(3-hydroxy-1-propynyl)-4-thioxothieno[2,3-b]pyridin-7(4H)-yl]acetic acid;

(20) N-(4-Chlorobenzyl)-7-ethyl-2-(4-hydroxybutyl)-4-thioxo-4,7-dihydrothieno[2,3-b]pyridine-5-carboxamide;
(21) N-(4-Chlorobenzyl)-7-(2-hydroxyethyl)-2-(3-hydroxypropyl)-4-thioxo-4,7-dihydrothieno[2,3-b]pyridine-5-carboxamide;
(22) N-(4-Chlorobenzyl)-7-[2-(diethylamino)ethyl]-2-(3-hydroxypropyl)-4-thioxo-4,7-dihydrothieno[2,3-b]pyridine-5-carboxamide;
(23) N-(4-Chlorobenzyl)-2-iodo-7-methyl-4-thioxo-4,7-dihydrothieno[2,3-b]-pyridine-5-carboxamide;
(24) N-(4-Chlorobenzyl)-2-(3-hydroxy-1-propynyl)-7-methyl-4-thioxo-4,7-dihydrothieno[2,3-b]pyridine-5-carboxamide;
(25) N-(4-Chlorobenzyl)-2-(3-hydroxypropyl)-7-methyl-4-thioxo-4,7-dihydrothieno[2,3-b]pyridine-5-carboxamide;
(26) N-(4-Chlorobenzyl)-2-iodo-7-isopropyl-4-thioxo-4,7-dihydrothieno[2,3-b]-pyridine-5-carboxamide;
(27) N-(4-Chlorobenzyl)-2-(3-hydroxy-1-propynyl)-7-isopropyl-4-thioxo-4,7-dihydrothieno[2,3-b]pyridine-5-carboxamide;
(28) N-(4-Chlorobenzyl)-2-(3-hydroxypropyl)-7-isopropyl-4-thioxo-4,7-dihydrothieno[2,3-b]pyridine-5-carboxamide;
(29) 4-{[3-(5-{[(4-Chlorobenzyl)amino]carbonyl}-7-ethyl-4-thidihydrothieno[2,3-b]pyridin-2-yl)-2-propynyl]oxy}-4-oxobutanoic acid;
(30) 3-(5-{[(4-Chlorobenzyl)amino]carbonyl}-7-ethyl-4-thioxo-4,7-dihydrothieno[2,3-b]pyridin-2-yl)-2-propynyl 2-(4-morpholinyl)acetate;
(31) 3-(5-{[(4-Chlorobenzyl)amino]carbonyl}-7-ethyl-4-thioxo-4,7-dihydrothieno[2,3-b]pyridin-2-yl)-2-propynyl 2-amino-3-methylbutanoate;
(32) 3-(5-{[(4-Chlorobenzyl)amino]carbonyl}-7-ethyl-4-thioxo-4,7-dihydrothieno[2,3-b]pyridin-2-yl)-2-propynyl 3-(4-morpholinylmethyl)benzoate;
(33) N-(4-chlorobenzyl)-2-(hydroxymethy)-7-methyl-4-thioxo-4,7-dihydrothienol[2,3-b]pyridine-5-carboxamide;
(34) N-(4-chlorobenzyl)-7-methyl-2-(4-morpholinylmethyl)-4-thioxo-4,7-dihydrothienol[2,3-b]pyridine-5-carboxamide;
(35) N-(4-chlorobenzyl)-7-methyl-2-(4-morpholinylmethyl)-4-thioxo-4,7-dihydrothieno[2,3-b]pyridine-5-carboxamide;
(36) N-(4-chlorobenzyl)-7-methyl-4-thioxo-2-(4-thiomorpholinylmethyl)-4,7-dihydrothieno [2,3-b]pyridine-5-carboxamide;
(37) N-(4-chlorobenzyl)-2-(((2-hydroxy-2-(4-hydroxyphenyl)ethyl)-(methyl)amino)methyl)-7-methyl-4-thioxo-4,7-dihydrothieno[2,3-b]pyridine-5-carboxamide;
(38) N-(4-chlorobenzyl)-2-(((2-hydroxy-2-phenylethyl)(methyl)-amino)methyl)-7-methyl-4-thioxo-4,7-dihydrothieno[2,3-b]pyridine-5-carboxamide;
(39) N-(4-chlorobenzyl)-4-mercapto-2-(4-morpholinylmethyl)thieno[2,3-b]pyridine-5-carboxamide;
(40) N-(4-Chlorobenzyl)-7-ethyl-2-(4-morpholinylmethyl)-4-thioxo-4,7-dihydrothieno[2,3-b]pyridine-5-carboxamide;
(41) N-(4-Chlorobenzyl)-2-(4-morpholinylmethyl)-4-thioxo-7-propyl-4,7-dihydrothieno[2,3-b]pyridine-5-carboxamide;
(42) N-(4-Chlorobenzyl)-7-isopropyl-2-(4-morpholinylmethyl)-4-thioxo-4,7-dihydrothieno[2,3-b]pyridine-5-carboxamide;
(43) N-(4-Fluorobenzyl)-7-methyl-2-(4-morpholinylmethyl)-4-thioxo-4,7-dihydrothieno[2,3-b]pyridine-5-carboxamide;
(44) N-(4-bromobenzyl)-7-methyl-2-(4-morpholinylmethyl)-4-thioxo-4,7-dihydrothieno[2,3-b]pyridine-5-carboxarnide;
(45) N-(4-chlorobenzyl)-7-methyl-2-(4-morpholinylcarbonyl)-4-thioxo-4,7-dihydrothieno[2,3-b]pyridine-5-carboxamide;
(46) 7-Benzyl-N-(4-chlorobenzyl)-2-(4-morpholinylmethyl)-4-thioxo-4,7-dihydrothieno[2,3-b]pyridine-5-carboxamide;
(47) N-(4-Chlorobenzyl)-7-(3-fluorobenzyl)-2-(4-morpholinylmethyl)-4-thioxo-4,7-dihydrothieno[2,3-b]pyridine-5-carboxamide;
(48) N-(4-Chlorobenzyl)-2-(4-morpholinylmethyl)-4-thioxo-7-(3-phenylpropyl)-4,7-dihydrothieno[2,3-b]pyridine-5-carboxamide;
(49) N-(4-Chlorobenzyl)-2-(4-morpholinylmethyl)-4-thioxo-7-(tetrahydro-2-furanylmethyl)-4,7-dihydrothieno[2,3-b]pyridine-5-carboxarnide;
(50) N-(4-Chlorobenzyl)-2-(4-morpholinylmethyl)-4-thioxo-7-[2-(1-pyrrolidinyl)ethyl]-4,7-dihydrothieno[2,3-b]pyridine-5-carboxamide;
(51) N-(4-Chlorobenzyl)-2-(4-morpholinylmethyl)-4-thioxo-7-(3-pyridinylmethyl)-4,7-dihydrothieno[2,3-b]pyridine-5-carboxamide;
(52) N-(4-Chlorobenzyl)-2-(4-morpholinylmethyl)-4-thioxo-7-(4-pyridinylmethyl)-4,7-dihydrothieno[2,3-b]pyridine-5-carboxamide;
(53) Methyl-5-({[4-chlorobenzyl)amino]carbonyl}-4-mercaptothienol[2,3-b]pyridine-2-carboxylate;
(54) N-(4-Chlorobenzyl)-4-mercapto-2-(hydroxymethyl)thieno[2,3-b]pyridine-5-carboxamide; or
(55) N-(4-chlorobenzyl)-4-mercapto-2-(4-morpholinylcarbonyl)thieno[2,3-b]pyridine-5-carboxamide; or a pharmaceutically acceptable salt thereof.

19. The compound of claim 1 which is:
(1) N-(4-Chlorobenzyl)-7-ethyl-2-(3-hydroxy-1-propynyl)-4-thioxo-4,7-dihydro-thieno[2,3-b]pyridine-5-carboxamide;
(2) N-(4-Chlorobenzyl)-7-ethyl-2-(4-hydroxy-1-butynyl)-4-thioxo-4,7-dihydro-thieno[2,3-b]pyridine-5-carboxamide;
(3) N-(4-Chlorobenzyl)-7-ethyl-2-(3-hydroxypropyl)-4-thioxo-4,7-dihydro-thieno[2,3-b]pyridine-5-carboxamide;
(4) N-(4-Chlorobenzyl)-7-(2-hydroxyethyl)-2-(3-hydroxy-1-propynyl)-4-thioxo-4,7-dihydrothieno[2,3-b]pyridine-5-carboxamide;
(5) N-(4-Chlorobenzyl)-7-[2-(diethylamino)ethyl]-2-(3-hydroxy-1-propynyl)-4-thioxo-4,7-dihydrothieno[2,3-b]pyridine-5-carboxamide;
(6) N-(4-Chlorobenzyl)-7-ethyl-2-(4-hydroxybutyl)-4-thioxo-4,7-dihydro-thieno[2,3-b]pyridine-5-carboxamide;
(7) N-(4-Chlorobenzyl)-7-(2-hydroxyethyl)-2-(3-hydroxypropyl)-4-thioxo-4,7-dihydrothieno[2,3-b]pyridine-5-carboxamide;

(8) N-(4-Chlorobenzyl)-7-[2-(diethylamino)ethyl]-2-(3-hydroxypropyl)-4-thioxo-4,7-dihydrothieno[2,3-b]pyridine-5-carboxamide;
(9) N-(4-Chlorobenzyl)-2-iodo-7-methyl-4-thioxo-4,7-dihydrothieno[2,3-b]-pyridine-5-carboxamide;
(10) N-(4-Chlorobenzyl)-2-(3-hydroxy-1-propynyl)-7-methyl-4-thioxo-4,7-dihydrothieno[2,3-b]pyridine-5-carboxamide;
(11) N-(4-Chlorobenzyl)-2-(3-hydroxypropyl)-7-methyl-4-thioxo-4,7-dihydro-thieno[2,3-b]pyridine-5-carboxamide;
(12) N-(4-Chlorobenzyl)-2-iodo-7-isopropyl-4-thioxo-4,7-dihydrothieno[2,3-b]-pyridine-5-carboxamide;
(13) N-(4-Chlorobenzyl)-2-(3-hydroxy-1-propynyl)-7-isopropyl-4-thioxo-4,7-dihydrothieno[2,3-b]pyridine-5-carboxamide;
(14) N-(4-Chlorobenzyl)-2-(3-hydroxypropyl)-7-isopropyl-4-thioxo-4,7-dihydro-thieno[2,3-b]pyridine-5-carboxamide;
(15) 4-{[3-(5-{[(4-Chlorobenzyl)amino]carbonyl}-7-ethyl-4-thioxo-4,7-dihydro-thieno[2,3-b]pyridin-2-yl)-2-propynyl]oxy}-4-oxobutanoic acid;
(16) 3-(5-{[(4-Chlorobenzyl)amino]carbonyl}-7-ethyl-4-thioxo-4,7-dihydro-thieno[2,3-b]pyridin-2-yl)-2-propynyl 2-(4-morpholinyl)acetate;
(17) 3-(5-{[(4-Chlorobenzyl)amino]carbonyl}-7-ethyl-4-thioxo-4,7-dihydro-thieno[2,3-b]pyridin-2-yl)-2-propynyl 2-amino-3-methylbutanoate;
(18) 3-(5-{[(4-Chlorobenzyl)amino]carbonyl}-7-ethyl-4-thioxo-4,7-dihydro-thieno[2,3-b]pyridin-2-yl)-2-propynyl 3-(4-morpholinylmethyl)benzoate;
(19) N-(4-chlorobenzyl)-7-methyl-2-(4-morpholinylmethyl)-4-thioxo-4,7-dihydrothienol[2,3-b]pyridine-5-carboxamide;
(20) N-(4-chlorobenzyl)-7-methyl-2-(4-morpholinylmethyl)-4-thioxo-4,7-dihydrothieno[2,3-b]pyridine-5-carboxamide;
(21) N-(4-chlorobenzyl)-7-methyl-4-thioxo-2-(4-thiomorpholinylmethyl)-4,7-dihydrothieno[2,3-b]pyridine-5-carboxamide;
(22) N-(4-chlorobenzyl)-2-(((2-hydroxy-2-(4-hydroxyphenyl)ethyl)-(methyl)amino)methyl)-7-methyl-4-thioxo-4,7-dihydrothieno[2,3-b]pyridine-5-carboxamide;
(23) N-(4-chlorobenzyl)-2-(((2-hydroxy-2-phenylethyl)(methyl)amino)methyl)-7-methyl-4-thioxo-4,7-dihydrothieno[2,3-b]pyridine-5-carboxamide;
(24) N-(4-Chlorobenzyl)-7-ethyl-2-(4-morpholinylmethyl)-4-thioxo-4,7-dihydrothieno[2,3-b]pyridine-5-carboxamide;
(25) N-(4-Chlorobenzyl)-2-(4-morpholinylmethyl)-4-thioxo-7-propyl-4,7-dihydrothieno[2,3-b]pyridine-5-carboxamide;
(26) N-(4-Chlorobenzyl)-7-isopropyl-2-(4-morpholinylmethyl)-4-thioxo-4,7-dihydrothieno[2,3-b]pyridine-5-carboxamide;
(27) N-(4-Fluorobenzyl)-7-methyl-2-(4-morpholinylmethyl)-4-thioxo-4,7-dihydrothieno[2,3-b]pyridine-5-carboxamide;
(28) N-(4-bromobenzyl)-7-methyl-2-(4-morpholinylmethyl)-4-thioxo-4,7-dihydrothieno[2,3-b]pyridine-5-carboxamide;
(29) 7-Benzyl-N-(4-chlorobenzyl)-2-(4-morpholinylmethyl)-4-thioxo-4,7-dihydrothieno[2,3-b]pyridine-5-carboxamide;
(30) N-(4-Chlorobenzyl)-7-(3-fluorobenzyl)-2-(4-morpholinylmethyl)-4-thioxo-4,7-dihydrothieno[2,3-b]pyridine-5-carboxamide;
(31) N-(4-Chlorobenzyl)-2-(4-morpholinylmethyl)-4-thioxo-7-(3-phenylpropyl)-4,7-dihydrothieno[2,3-b]pyridine-5-carboxamide;
(32) N-(4-Chlorobenzyl)-2-(4-morpholinylmethyl)-4-thioxo-7-(tetrahydro-2-furanylmethyl)-4,7-dihydrothieno[2,3-b]pyridine-5-carboxamide;
(33) N-(4-Chlorobenzyl)-2-(4-morpholinylmethyl)-4-thioxo-7-[2-(1-pyrrolidinyl)ethyl]-4,7-dihydrothieno[2,3-b]pyridine-5-carboxamide;
(34) N-(4-Chlorobenzyl)-2-(4-morpholinylmethyl)-4-thioxo-7-(3-pyridinylmethyl)-4,7-dihydrothieno[2,3-b]pyridine-5-carboxamide; or
(35) N-(4-Chlorobenzyl)-2-(4-morpholinylmethyl)-4-thioxo-7-(4-pyridinylmethyl)-4,7-dihydrothieno[2,3-b]pyridine-5-carboxamide; or a pharmaceutically acceptable salt thereof.

20. The compound of claim 1 which is:
(1) N-(4-Chlorobenzyl)-7-ethyl-2-(3-hydroxy-1-propynyl)-4-thioxo-4,7-dihydro-thieno[2,3-b]pyridine-5-carboxamide;
(2) N-(4-Chlorobenzyl)-7-ethyl-2-(4-hydroxy-1-butynyl)-4-thioxo-4,7-dihydro-thieno[2,3-b]pyridine-5-carboxamide;
(3) N-(4-Chlorobenzyl)-7-ethyl-2-(3-hydroxypropyl)-4-thioxo-4,7-dihydro-thieno[2,3-b]pyridine-5-carboxamide;
(4) N-(4-Chlorobenzyl)-7-(2-hydroxyethyl)-2-(3-hydroxy-1-propynyl)-4-thioxo-4,7-dihydrothieno[2,3-b]pyridine-5-carboxamide;
(5) N-(4-Chlorobenzyl)-7-[2-(diethylamino)ethyl]-2-(3-hydroxy-1-propynyl)-4-thioxo-4,7-dihydrothieno[2,3-b]pyridine-5-carboxamide;
(6) N-(4-Chlorobenzyl)-7-ethyl-2-(4-hydroxybutyl)-4-thioxo-4,7-dihydro-thieno[2,3-b]pyridine-5-carboxamide;
(7) N-(4-Chlorobenzyl)-7-(2-hydroxyethyl)-2-(3-hydroxypropyl)-4-thioxo-4,7-dihydrothieno[2,3-b]pyridine-5-carboxamide;
(8) N-(4-Chlorobenzyl)-7-[2-(diethylamino)ethyl]-2-(3-hydroxypropyl)-4-thioxo-4,7-dihydrothieno[2,3-b]pyridine-5-carboxamide;
(9) N-(4-Chlorobenzyl)-2-iodo-7-methyl-4-thioxo-4,7-dihydrothieno[2,3-b]-pyridine-5-carboxamide;
(10) N-(4-Chlorobenzyl)-2-(3-hydroxy-1-propynyl)-7-methyl-4-thioxo-4,7-dihydrothieno[2,3-b]pyridine-5-carboxamide;
(11) N-(4-Chlorobenzyl)-2-(3-hydroxypropyl)-7-methyl-4-thioxo-4,7-dihydro-thieno[2,3-b]pyridine-5-carboxamide;
(12) N-(4-Chlorobenzyl)-2-iodo-7-isopropyl-4-thioxo-4,7-dihydrothieno[2,3-b]-pyridine-5-carboxamide;
(13) N-(4-Chlorobenzyl)-2-(3-hydroxy-1-propynyl)-7-isopropyl-4-thioxo-4,7-dihydrothieno[2,3-b]pyridine-5-carboxamide;
(14) N-(4-Chlorobenzyl)-2-(3-hydroxypropyl)-7-isopropyl-4-thioxo-4,7-dihydro-thieno[2,3-b]pyridine-5-carboxamide;
(15) N-(4-chlorobenzyl)-7-methyl-2-(4-morpholinylmethyl)-4-thioxo-4,7-dihydrothieno[2,3-b]pyridine-5-carboxamide;

(16) N-(4-chlorobenzyl)-7-methyl-2-(4-morpholinylmethyl)-4-thioxo-4,7-dihydrothieno[2,3-b]pyridine-5-carboxamide;

(17) N-(4-chlorobenzyl)-7-methyl-4-thioxo-2-(4-thiomorpholinylmethyl)-4,7-dihydrothieno[2,3-b]pyridine-5-carboxamide;

(18) N-(4-chlorobenzyl)-2-(((2-hydroxy-2-(4-hydroxyphenyl)ethyl)-(methyl)amino)methyl)-7-methyl-4-thioxo-4,7-dihydrothieno[2,3-b]pyridine-5-carboxamide;

(19) N-(4-chlorobenzyl)-2-(((2-hydroxy-2-phenylethyl)(methyl)-amino)methyl)-7-methyl-4-thioxo-4,7-dihydrothieno[2,3-b]pyridine-5-carboxarnide;

(20) N-(4-Chlorobenzyl)-7-ethyl-2-(4-morpholinylmethyl)-4-thioxo-4,7-dihydrothieno[2,3-b]pyridine-5-carboxamide;

(21) N-(4-Chlorobenzyl)-2-(4-morpholinylmethyl)-4-thioxo-7-propyl-4,7-dihydrothieno[2,3-b]pyridine-5-carboxamide;

(22) N-(4-Chlorobenzyl)-7-isopropyl-2-(4-morpholinylmethyl)-4-thioxo-4,7-dihydrothieno[2,3-b]pyridine-5-carboxamide;

(23) N-(4-Fluorobenzyl)-7-methyl-2-(4-morpholinylmethyl)-4-thioxo-4,7-dihydrothieno[2,3-b]pyridine-5-carboxamide;

(24) N-(4-bromobenzyl)-7-methyl-2-(4-morpholinylmethyl)-4-thioxo-4,7-dihydrothieno[2,3-b]pyridine-5-carboxamide;

(25) $^7$-Benzyl-N-(4-chlorobenzyl)-2-(4-morpholinylmethyl)-4-thioxo-4,7-dihydrothieno[2,3-b]pyridine-5-carboxamide;

(26) N-($^4$-Chlorobenzyl)-7-(3-fluorobenzyl)-2-(4-morpholinylmethyl)-4-thioxo-4,7-dihydrothieno[2,3-b]pyridine-5-carboxamide;

(27) N-($^4$-Chlorobenzyl)-2-(4-morpholinylmethyl)-4-thioxo-7-(tetrahydro-2-furanylmethyl)-4,7-dihydrothieno[2,3-b]pyridine-5-carboxamide;

(28) N-(4-Chlorobenzyl)-2-(4-morpholinylmethyl)-4-thioxo-7-[2-(1-pyrrolidinyl)ethyl]-4,7-dihydrothieno[2,3-b]pyridine-5-carboxamide;

(29) N-(4-Chlorobenzyl)-2-(4-morpholinylmethyl)-4-thioxo-7-(3-pyridinylmethyl)-4,7-dihydrothieno[2,3-b]pyridine-5-carboxamide; or

(30) N-(4-Chlorobenzyl)-2-(4-morpholinylmethyl)-4-thioxo-7-(4-pyridinylmethyl)-4,7-dihydrothieno[2,3-b]pyridine-5-carboxamide; or a pharmaceutically acceptable salt thereof.

21. The compound of claim 1 which is:

(1) N-(4-Chlorobenzyl)-7-[2-(diethylamino)ethyl]-2-(3-hydroxypropyl)-4-thioxo-4,7-dihydrothieno[2,3-b]pyridine-5-carboxamide;

(2) N-(4-Chlorobenzyl)-2-(3-hydroxy-1-propynyl)-7-methyl-4-thioxo-4,7-dihydro-thieno [2,3-b]pyridine-5-carboxamide;

(3) N-(4-Chlorobenzyl)-2-(3-hydroxypropyl)-7-methyl-4-thioxo-4,7-dihydro-thieno[2,3-b]pyridine-5-carboxamide;

(4) N-(4-chlorobenzyl)-7-methyl-2-(4-morpholinylmethyl)-4-thioxo-4,7-dihydrothieno[2,3-b]pyridine-5-carboxamide;

(5) N-(4-chlorobenzyl)-2-(((2-hydroxy-2-(4-hydroxyphenyl)ethyl)(methyl)-amino)methyl)-7-methyl-4-thioxo-4,7-dihydrothieno[2,3-b]pyridine-5-carboxamide;

(6) N-(4-chlorobenzyl)-2-(((2-hydroxy-2-phenylethyl)(methyl)-amino)methyl)-7-methyl-4-thioxo-4,7-dihydrothieno[2,3-b]pyridine-5-carboxamide;

(7) N-(4-Chlorobenzyl)-7-ethyl-2-(4-morpholinylmethyl)-4-thioxo-4,7-dihydrothieno[2,3-b]pyridine-5-carboxamide; or (8) N-(4-Chlorobenzyl)-2-(4-morpholinylmethyl)-4-thioxo-7-propyl-4,7-dihydrothieno[2,3-b]pyridine-5-carboxarnide; or a pharmaceutically acceptable salt thereof.

22. The compound N-(4-chlorobenzyl)-7-methyl-2-(4-morpholinylmethyl)-4-thioxo-4,7-dihydrothieno[2,3-b]pyridine-5-carboxamide or a pharmaceutically acceptable salt thereof.

23. A pharmaceutical composition comprising a compound of claim 1 and a pharmaceutically acceptable excipient.

24. A method for treating a herpesviral infection, comprising administering to a mammal in need of such treatment, an effective amount of a compound of claim 1.

25. The method of claim 24 wherein the herpesviral infection is herpes simplex virus type 1, 2, 6, 7, or 8, varicella zoster virus, human cytomegalovirus, or Epstein-Barr virus.

26. The method of claim 24 wherein the herpesviral infection is herpes simplex virus type 1, herpes simplex Virus type 2, varicella zoster virus, human cytomegalovirus, Epstein-Barr virus, human herpes viruses 7 or human herpes viruses 8.

27. The method of claim 24 wherein the herpesviral infection is human cytomegalovirus.

28. A method for treating atherosclerosis or restenosis, comprising administering to a mammal in need of such treatment, an effective amount of a compound of claim 1.

29. A method for inhibiting a viral DNA polymerase comprising contacting the polymerase with an effective inhibitory amount of a compound of claim 1.

30. A method for preparing a thioxo compound of formula I:

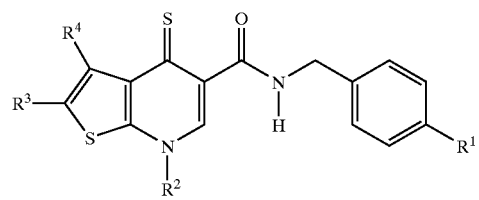

wherein $R^1$–$R^4$ have the values in claim 1, comprising reacting a corresponding oxo compound of the formula II:

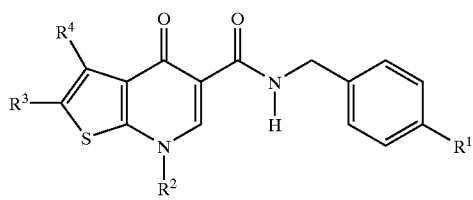

with a suitable thionating reagent to provide the compound of formula I.

* * * * *

UNITED STATES PATENT AND TRADEMARK OFFICE
CERTIFICATE OF CORRECTION

PATENT NO. : 6,620,810 B2
DATED : September 16, 2003
INVENTOR(S) : Atli Thorarensen It is certified that error appears in the above-identified patent and that said Letters Patent is hereby corrected as shown below:

Column 23,
Line 7, delete ")" after "$CO_2R^{14}$".

Column 24,
Line 40, delete "(" after "2-[3-(5-".
Line 53, delete "--" and insert -- -1- -- therefor.

Column 25,
Line 28, delete "thidihydrothieno" and insert -- thioxo-4,7-dihydrothieno -- therefor.

Column 26,
Line 36, delete "(" after "Methyl-5-".
Line 36, insert -- ( -- before "4-chlorobenzyl".

Column 29,
Line 31, delete "$^7$-Benzyl" and insert -- 7-Benzyl -- therefor.
Lines 34 and 37, delete "$^4$-Chlorobenzyl" and insert -- 4-Chlorobenzyl -- therefor.

Signed and Sealed this

Twenty-third Day of March, 2004

JON W. DUDAS
*Acting Director of the United States Patent and Trademark Office*